(12) United States Patent
Waxman et al.

(10) Patent No.: US 8,774,905 B2
(45) Date of Patent: Jul. 8, 2014

(54) METHODS FOR DETECTION OF VULNERABLE PLAQUE WITH QUANTITATIVE COLORIMETRY DURING ANGIOSCOPY

(75) Inventors: Sergio Waxman, Newton, MA (US); Fumiyuki Ishibashi, Fukuoka (JP)

(73) Assignee: Lahey Clinic Foundation, Inc., Burlington, MA (US)

( * ) Notice: Subject to any disclaimer, the term of this patent is extended or adjusted under 35 U.S.C. 154(b) by 899 days.

(21) Appl. No.: 12/675,439

(22) PCT Filed: Aug. 29, 2008

(86) PCT No.: PCT/US2008/010267
§ 371 (c)(1),
(2), (4) Date: Jul. 15, 2010

(87) PCT Pub. No.: WO2009/032206
PCT Pub. Date: Mar. 12, 2009

(65) Prior Publication Data
US 2010/0278735 A1    Nov. 4, 2010

Related U.S. Application Data (60) Provisional application No. 60/966,836, filed on Aug. 30, 2007.

(51) Int. Cl.
*A61B 5/02* (2006.01)
(52) U.S. Cl.
USPC ............ 600/479; 600/475; 600/476; 600/478

(58) Field of Classification Search
USPC .................................. 600/475–476, 478–479
See application file for complete search history.

(56) References Cited

U.S. PATENT DOCUMENTS

| | | | |
|---|---|---|---|
| 2001/0047137 A1* | 11/2001 | Moreno et al. | 600/475 |
| 2004/0077950 A1 | 4/2004 | Marshik-Geurts | |
| 2005/0030372 A1 | 2/2005 | Jung et al. | |
| 2007/0038124 A1* | 2/2007 | Fulghum et al. | 600/476 |

OTHER PUBLICATIONS

Balas, (An Imaging Colorimeter for Noncontact Tissue Color Mapping), IEEE Transactions Om Biomedical Engineering, vol. 44, No. 6, Jun. 1997.*

Ogawa et al. (Application of 18F-FDG PET for Monitoring the Therapeutic Effect of Anti-inflammatory Drugs on Stabilization of Vulnerable Atherosclerotic Plaques), J Nucl Med 2006; 47: 1845-1850.*

Okada et al., Plaque Color Analysis by the Conventional Yellow-Color Grading System and Quantitative Measurement Using LCH Color Space, Journal of Interventional Cardiology, vol. 20, No. 5, 2007.*

PCTISA210, US, A1, Nov. 3, 2008, Waxman et al.

(Continued)

*Primary Examiner* — Long V. Le
*Assistant Examiner* — Ellsworth Weatherby
(74) *Attorney, Agent, or Firm* — Lawson & Weitzen, LLP; Sonia K. Guterman; Anna E. Stanford (57) ABSTRACT

Methods are provided for detecting lipid cores underneath thin fibrous caps (LCTC) and thin-cap fibroatheromas (TCFA) in a subject in need of diagnosis for having a vulnerable plaque, a plaque at risk of disruption or thrombosis, or risk of an acute coronary syndrome, and for screening compounds for modulators of this process.

17 Claims, 5 Drawing Sheets

(56) References Cited

OTHER PUBLICATIONS

Arakawa et al. 2002 Arterioscler Thromb Vasc Biol 22: 1002-1007.
Asakura et al. 2001 J Am Coll Cardiol 37: 1284-1288.
Blankenhorn et al. 1956 J Clin Invest 35: 1243-1247.
de Feyter et al. 1995 Circulation 92: 1408-1413.
Goldstein et al. 2000 N Engl J Med 343: 915-922.
Goulinet et al. 1997 Arterioscler Thromb Vasc Biol 17: 786-796.
Hong et al. 2004 Circulation 110: 928-933.
Ishibashi et al. 2007 Am J Cardiol 100: 1207-1211.
Ishibashi et al. 2007 Int J Cardiovasc Imaging 23: 679-691.
Ishibashi et al. 2008 J Am Coll Cardiol 51: B26 (2900-16).
Isoda et al. 2001 Int J Angiol 10: 183-187.
Kolodgie et al. 2003 New Engl J Med 349: 2316-2325.
Lehmann et al. 1997 Circulation 96: 3030-3041.
Lehmann et al. 1998 Catheter Cardiovasc Diag 45: 191-201.
Libby 2005 J Am Coll Cardiol 45: 1600-1602.
Libby et al. 2006 J Am Coll Cardiol 48: A33-A46.
Mauriello et al. 2005 J Am Coll Cardiol 45: 1585-1593.
Miyamoto et al. 2004 Clin Cardiol 27: 9-15.
Mizuno et al. 1991 Lancet 337: 809-812.
Okamatsu et al. 2004 Circulation 109: 465-470.
Rioufol et al. 2002 Circulation 106: 804-808.
Sakai et al. 2003 J Am Coll Cardiol 42: 1558-1565.
Schoenhagen et al. 2003 Arterioscler Thromb Vasc Biol 23: 1895-1900.
Small 1988 Arterioscler 8: 103-129.
Stary et al. 1995 Circulation 92: 1355-1374.
Takano et al. 2003 J Am Coll Cardiol 42: 680-686.
Takano et al. 2005 J Am Coll Cardiol 45: 652-658.
Tanaka et al. 2005 J Am Coll Cardiol 45: 1594-1599.
Thieme et al. 1996 J Am Coll Cardiol 28: 1-6.
Uchida et al. 1995 Am Heart J 130: 195-203.
Virmani et al. 2000 Arterioscler Thromb Vasc Biol 20: 1262-1275.
Waxman et al. 1997 Am J Cardiol 79: 1106-1109.
Waxman et al. 1996 Circulation 93: 2106-2113.
Waxman et al. 2006 Circulation 114: 2390-2411.

\* cited by examiner

METHODS FOR DETECTION OF VULNERABLE PLAQUE WITH QUANTITATIVE COLORIMETRY DURING ANGIOSCOPY

RELATED APPLICATIONS

The present application claims the benefit of U.S. provisional application Ser. No. 60/966,836 filed Aug. 30, 2007, and International application serial number PCT/US2008/010267 filed Aug. 29, 2008, each of which is hereby incorporated herein by reference in its entirety.

TECHNICAL FIELD

Methods are provided for detecting lipid cores underneath thin fibrous caps and measuring color of coronary or arterial plaque, to provide a diagnosis of risk for a condition such as vulnerable plaque, plaque at risk of disruption or thrombosis, thin-cap fibroatheromas and risk of acute coronary syndrome.

BACKGROUND

Heart disease is the leading cause of death for both men and women in this country, rising rapidly following menopause. Increased adiposity is implicated in the elevated risk of age-related metabolic disease in women, including heart diseases. The molecular and cell-biological mechanisms underlying the metabolic actions of various hormones and their relationship to adiposity are poorly understood. Advances in epidemiology, biochemistry and histological techniques show that lipid metabolism, particularly the metabolism of atherosclerotic plaque, is correlated with impending heart diseases.

Lehmann et al. (Lehmann K G et al. 1998 Cathet Cardiovasc Diagn 45:191-201) examined chromatic distortion during angioscopy using a quantitative colorimetric system with 2 color coordinates and HSI (hue, saturation, intensity) color space based on the tri-stimulus values mimicking the human color vision. In another study (Lehmann K G, et al. 1997 Circulation 96:3030-3041), their system was utilized to differentiate thrombus based on color. However, the ability of their system to distinguish the color of atherosclerotic plaques, which have a different range of color from thrombus, is not known since this issue has not been investigated. In addition, for the detection of lipid cores under thin fibrous caps (LCTCs), two color coordinates used in these studies would be required to translate to a single coordinate of yellow color intensity.

Miyamoto et al (Miyamoto A et al. 2004. Clin Cardiol 27:9-15) used quantitative colorimetry to study the relation of yellow color saturation with the cap thickness of fibroatheromas, and found an inverse relationship by using color as a continuum rather than a binary measurement (yellow vs. white). In their system, yellow saturation, which is also derived from HSI color space, was used to represent yellow color intensity of plaques. However, yellow saturation may not ideally represent the gradations of yellow color intensity because of its nonlinear nature. In addition, no detailed process of optimization that considers the effects of variables was examined in their system.

Human carotid and femoral arteries are exemplary sites of plaque deposition and maturation, as a result of which a plaque is more likely to fracture and enter the circulating blood. There is a need for rapid, inexpensive and straightforward techniques of measuring and analyzing the condition of human atherosclerotic plaques, and applying such methods to assess the risk of coronary or arterial conditions.

SUMMARY

An embodiment of the invention herein provides a method for detecting lipid cores underneath thin fibrous caps (LCTC) and thin-cap fibroatheromas (TCFA) in a subject in need of diagnosis for having a vulnerable plaque, a plaque at risk of disruption or thrombosis, or risk of an acute coronary syndrome, having the steps of:

identifying a plurality of plaques in arteries of the subject during an angioscopy examination of the subject;

measuring parameters of location, morphology, size and thickness of the plaques; and applying a quantitative colorimetric method to measure coronary or arterial plaque color comprising L*a*b* color space determinants, wherein values of red color and yellow color yield a quantitative colorimetric parameter to detect LCTC and TCFA in the subject and provide a diagnosis of risk of at least one condition selected from the group of vulnerable plaque, plaque at risk of disruption or thrombosis, and risk of acute coronary syndrome. The color space determinants are defined as follows: a* is a green and red scale, and is scored from −100 to +100; b* is a blue and yellow scale, scored from −100 to +100; and L* is a brightness or black and white scale, scored from −100 to +100.

In a related embodiment, the method further involves, after applying the quantitative colorimetric method, comparing the values of red color and yellow color to respective values for positive controls having a condition selected from at least one of the group the of acute coronary syndrome, LCTC and TCFA. In another related embodiment, the method further involves, after applying the quantitative colorimetric method, comparing the values of red color and yellow color to respective values for negative controls lacking a history selected from at least one of the group of coronary or arterial syndromes, LCTC and TCFA. Applying the quantitative colorimetric method further can involve adjustment for brightness (L* value) to overcome variable factors known to affect the results in the angioscopy, such as background variables, and the factor is at least one variable selected from the group of intensity of light, angle and distance. The method involves angioscopy that is performed in a subject in vivo. Alternatively the angioscopy is performed in explanted cardiac tissue of a post-mortem sample.

Yet another embodiment of the invention herein provides a computer program embedded in a computer readable medium for analyzing quantitative colorimetric angioscopy data comprising L*a*b* color space determinants, wherein values of a red color and a yellow color yield a quantitative colorimetry to detect LCTC and TCFA.

Yet another embodiment of the invention herein, provides a method for analyzing colorimetric angioscopy, the improvement comprising applying a quantitative colorimetric method to measure coronary or arterial plaque color comprising L*a*b* color space determinants, wherein values of red color and yellow color yield a quantitative colorimetric parameter to detect LCTC and TCFA in the subject and provide a diagnosis of vulnerable plaque, a plaque at risk of disruption or thrombosis, or risk of an acute coronary syndrome.

In any of the above methods or computer programs, the subject is, for example, a male. Alternatively, the subject is a female. In general the subject is a human. In the embodiment in which the subject is a female, the subject can be, for example, post-menopausal or peri-menopausal.

Yet another embodiment of the invention provides a method for screening a plurality of test compounds to identify a modulator of formation of a plurality of coronary or arterial lipid core underneath thin fibrous caps (LCTC) or thin-cap fibroatheroma (TCFA) for administering to a subject at risk for a condition, the method comprising:

providing a plurality of animal subjects having at least one condition selected from the group of a vulnerable plaque, a plaque at risk of disruption or thrombosis, and risk of an acute coronary syndrome;

administering to a portion of the animals at least one test compound, and administering to another portion of the animals that are otherwise identical a control lacking the compound; and analyzing the arteries of each group of experimental animals with a quantitative colorimetric method to measure coronary or arterial plaque color comprising L*a*b* color space determinants, wherein values of red color and yellow color yield a quantitative colorimetry to detect LCTC and TCFA in the subject and provide a diagnosis of the at least one condition selected from the group of the vulnerable plaque, the plaque at risk of disruption or thrombosis, and the risk of acute coronary syndrome, such that the test compound that yields lower values of red color and yellow color, in the animals administered the compound compared to the control animals, is the potential modulator.

In any of the methods for detecting lipid cores under fibrous caps above, applying the quantitative colorimetric method further involves obtaining the diagnosis of risk for the condition from the value for each of the L*a*b* parameters, so that, for example, the risk is diagnosed when a* is greater than 0 and b* is greater than about 23, or a* is greater than about 15 and b* is greater than 0, and L has a value of about 40 to about 80. Alternatively, the risk is diagnosed when a* is greater than 0 (a positive number) and b* is greater than about 17, or about 20, or about 23, or about 26; or a* is greater than about 9, or about 12, or about 15, or about 18, or about 21, and b* is positive. In each case L has a value of about, for example, 40 to about 80, or about 35 to about 85, or about 35 to about 90, or about 40 to about 85.

The method provides the risk for the condition in the subject that is at least about 80%, at least about 85%, at least about 90%, or at least about 93% to 95%.

DETAILED DESCRIPTION

There has been a long felt need in the medical practice to predict acute coronary conditions, using for example, other imaging technologies for detection of thin-cap fibroatheromas, such as optical coherence tomography (OCT), ultrasound, near-infrared spectroscopy, intravascular magnetic resonance imaging. Accordingly, the present invention addresses a deficiency in the prior art. Among known color spaces which could be used for colorimetry, the International Committee on Illumination (CIE) 1976 color difference formula (L*a*b* color space) has been widely used to describe all the colors visible to the human eye. In this color space, yellow and red color intensity and brightness can be represented simply as positive b*, a*, and L* values, representing color intensity in a linear fashion. The application of this method makes objective color assessment possible.

The present invention describes the color values that are associated with potential vulnerable plaques and quantitates this color. A high yellow color intensity (HYCI) was observed for human carotid and femoral atherosclerotic plaques. This color is associated herein with the lipid cores underneath thin fibrous caps (LCTCs). High yellow color intensity (HYCI) of human carotid and femoral atherosclerotic plaques, determined by quantitative colorimetry during angioscopy, was associated with lipid cores underneath thin fibrous caps (LCTCs). To determine whether coronary HYCI regions are associated with LCTCs, the relationship of LCTCs with coronary surface color in human coronary autopsy specimens was investigated.

A quantitative colorimetric method was applied herein to angioscopy to measure coronary or arterial plaque color after proper adjustment for brightness, based on the L*a*b* color space. This method overcomes the effect of variables unique to angioscopy and creating a background effect, such variables being light intensity, angle of light, and distance, and eliminates the uncertainty of visual color assessment. By describing the colorimetric characteristics of such lesions as a measurable quantity, it has become possible to detect lipid cores underneath thin fibrous caps and thin-cap fibroatheromas, or vulnerable plaques, during angioscopic examination of the coronary arteries.

Previous applications of a quantitative colorimetric method to angioscopy based on the L*a*b* color space, are here found to require an adjustment for brightness to overcome certain limitations of color measurement during this type of procedure. The application of this method herein, to define the colorimetric characteristics of potentially vulnerable plaques, makes detection of vulnerable plaques possible with angioscopy or related imaging technologies.

The colorimetric characteristics of coronary lipid cores are described herein. These coronary lipid cores are located underneath thin (within 100 μm) fibrous caps (LCTC) and of thin-cap fibroatheromas (TCFA). Such plaques are considered to be the plaques-at-risk of thrombosis and of causing heart attacks, so called "vulnerable plaques". For this reason, quantitation of the risk arising from these plaques is of high medical importance.

Using this colorimetric method to analyze human coronary segments obtained from postmortem samples, and comparing with histology gold standard, a high yellow color intensity of a coronary plaque, is considered in a working example herein as having a quantitative cut-off of b*≥23, had a sensitivity and specificity of 90% and 77% for LCTC, and 93% and 70% for TCFA, respectively. Alternative embodiments of this quantitative cut-off are also provided herein as described below in the claims and Summary.

A different set of criteria that incorporated red color in addition to yellow color (b*>23, a*>0) or (b*>0, a*>15), was found herein to have a sensitivity and specificity of 95% and 97% for LCTC, and 93% and 90% for TCFA.

Thus, using these combinations in a quantitative colorimetry method applied to angioscopy was shown to be efficacious when used to detect LCTC and TCFA, which are considered to be the vulnerable plaques, and to determine risk of a variety of coronary or arterial pathologies.

This method could be used as the basis of a diagnostic tool for the detection of thin-cap fibroatheroma or vulnerable plaques. It could be applied to commercially available angioscopy systems and/or other emerging imaging technologies, such as ultrasound or near-infrared spectroscopy.

Vascular angioscopy systems are commercially manufactured, for example, from FiberTech Co., Ltd. (Markham, Ontario, Canada), and from InfraReDx, Inc., (Burlington, Mass.) which also manufactures a near-infrared spectroscopy catheter.

Additional embodiments and detailed description of examples are found in the following publications, firstly entitled, "High Yellow Color Intensity by Angioscopy with Quantitative Colorimetry to Identify High-Risk Features in Culprit Legions of Patients with Acute Coronary Syndromes", by Fumiyuki Ishibashi et al., published in American Journal of Cardiology 100:1207-1211, Oct. 15, 2007 which is hereby incorporated herein in its entirety; and in a portion of this work published as an abstract by Ishibashi F et al., entitled, "Quantitative Colorimetry of Coronary Thin Cap Fibroatheroma in Human Autopsy Specimens." JACC Cardiovascular Interventions 2008; 1(Supplement B):B26, which also is incorporated herein by reference in its entirety; and in a paper entitled, "Quantitative Colorimetry of Atherosclerotic Plaque Using the L*a*b* Color Space During Angioscopy For the Detection of Lipid Cores Underneath Thin Fibrous Caps", by Fumiyuki Ishibashi et al., published in International Journal of Cardiovascular Imaging 23(6), 679-691 December 2007, and which also is incorporated herein by reference in its entirety.

Further exemplification is found in the Examples and claims herein, which are exemplary only and are not to be construed as further limiting the scope of the invention.

Angioscopy was performed in 40 non-severely stenotic coronary segments dissected from 17 autopsy hearts. Histopathology slides (1045) were prepared at 2 mm intervals for morphometry and measurement. Luminal surface diagrams of coronary segments were constructed from histology to compare with angioscopic images. The relation of LCTCs (consecutive surface regions of lipid cores underneath fibrous cap<100 μm) with surface color measured during angioscopy using quantitative colorimetry with the L*a*b* color space (positive a* and b*: yellow and red) was examined. The predominant histologic plaque types observed in 21 LCTCs were thin-cap fibroatheroma (TCFA, n=14), fibroatheroma (n=2) and fibrocalcific plaque (n=5). A predefined HYCI (b*≥23) was identified in 19 (90%) of 21 LCTCs as compared with 14 (23%) of 60 non-LCTCs (p<0.0001). The color (a*, b*) was (7.04±1.52, 29.48±1.52) in 21 LCTCs. In 81 angioscopic regions, the sensitivity and specificity of (a*>0, b*>23) or (a*>15, b*>0) for LCTCs were 95% and 97%, and for TCFAs were 93% and 90%, respectively. From the data, HYCI was concluded to be associated with LCTCs in ex-vivo human coronaries. Coronary LCTCs may be reliably characterized as high yellow/red color intensity regions by angioscopy with quantitative colorimetry.

Coronary lipid cores underneath thin fibrous caps, which are associated with culprit lesions underlying acute coronary syndromes (ACS) [Libby P et al. 2006 J Am Coll Cardiol 48:A33-46], may appear yellow by coronary angioscopy. This is based on the clinical studies demonstrating the association between yellow plaques and culprit lesions of ACS [Mizuno K et al. 1991 Lancet 337:809-812; de Feyter P J et al. 1995 Circulation. 92:1408-1413; Waxman S et al. 1996 Circulation. 93:2106-2113; Sakai S et al. 2003 J Am Coll Cardiol. 42:1558-1565] or thrombus [Waxman S et al. 1997 Am J Cardiol 79:1106-1109; Okamatsu K et al. 2004 Circulation 109:465-470; Takano M et al. 2005 J Am Coll Cardiol. 45:652-658], as well as the histopathologic studies in which yellow plaques are associated with atheromatous plaques [Uchida Y et al. 1995 Am Heart J 1995; 130:195-203; Thieme T et al. 1996 J Am Coll Cardiol 28:1-6; Isoda K et al. 2001 Int J Angiology 10:183-187]. Since several factors can affect color perception during angioscopy, such as intensity of light, angle or distance [Lehmann K G et al. 1998 Cathet Cardiovasc Diagn 45:191-201; Miyamoto A et al. 2004 Clin Cardiol 27:9-15], the examples herein applied a quantitative colorimetric method to angioscopy to measure coronary plaque color after proper adjustment for brightness, which overcomes these variables and eliminates the uncertainty of visual assessments [Ishibashi F et al. 2007 Int J Cardiovasc Imaging 23:679-691 incorporated herein by reference]. In ex-vivo tissue samples excised during endoarterectomy of human carotid/femoral arteries, high yellow color intensity (HYCI), determined by this quantitative method, was associated with lipid cores underneath "thin" fibrous caps (cap thickness<100 μm, LCTCs) [Ibid.] Therefore, this association may be similar in human coronary arteries.

To determine whether coronary HYCI regions are associated with LCTCs, the relationship of LCTCs with coronary surface color in human coronary artery autopsy specimens using angioscopy was investigated herein with the quantitative colorimetric method.

EXAMPLES

Example 1

Sample Preparation

Coronary arteries of 17 patients (mean age: 65±3 years, 13 males and 4 females) were used within 48 hours postmortem. The cause of death in these patients was: ACS (n=3); multiple organ failure (n=5); cerebrovascular disease (n=6); and unknown (n=3). The arteries were examined in situ with a 4.5F angioscope catheter (Vecmova, Clinical Supply Co., Gifu, Japan) with xenon lamplight to eliminate the severely stenotic or occluded segments.

Following initial angioscopic examination, 40 non-severely stenotic segments [1 segment/proximal to mid portion of 1 coronary, mean length: 52±3 mm, right coronary artery (RCA, n=15), left main trunk and left anterior descending artery (LMT+LAD, n=13), left circumflex artery (LCX, n=12)] were dissected from the hearts. Each segment was mounted in a cage after ligating the side branches, and both ends of each segment were attached to the connectors and placed in a physiological saline solution bath.

Example 2

Angioscopic Image Acquisition and Procedure

The system used angioscope catheters, a xenon lamplight source (Baxter OPTX 300, Baxter Laboratories, Irvine, Calif.), a charge-coupled device (CCD) camera (Baxter OPTX 5000, Baxter laboratories) with National Television System Committee (NTSC) color system and a television monitor. When white balancing, dry white paint oil (Pure White of Designers Gouache, Winsor & Newton, London, UK) was used. Light intensity was adjusted to the maximum to enhance the white color at the periphery of the image field.

Each segment was pressurized at 80-120 mmHg with pulsatile saline flow (100-130 mL/min). An angioscope catheter was advanced into the distal end of a segment using a 0.014 inch guidewire, and was manually pulled back from the distal to the proximal end of the segment. During the pull-back of the catheter, brightness of an image field was adjusted visually by manipulating light intensity or the distance from the catheter to the vessel surface. A DVD player/recorder (DMR-ES25SXX, Panasonic Corporation of North America, Secaucus, N.J.) was directly connected with the CCD camera using S (Y/C) signal output/input, and all images were recorded to a DVD disc.

Example 3

Histopathology Process of Sample

After the angioscopic procedure, the coronary segments were pressure-fixed (80 mm Hg) and decalcified. Each segment was cut perpendicular to the long axis of the vessel at 2 mm intervals. A total of 1045 (×2) histopathology slides with 5 μm tissue slices for each tissue with 2 mm length was prepared (one each for Hematoxilin-Eosin stain and for Russell-Movat's pentachrome stain).

Example 4

Histopathology Image Analysis

Since angioscopy provides only information of subsurface structures and not of the entire lesion because of the limited penetration of light into the tissues [Miyamoto A et al. 2004 Clin Cardiol 27:9-15, Ishibashi F et al. 2007 Int J Cardiovasc Imaging 23:679-691], cross-sectional images of tissue slices could not be directly used to compare with angioscopic images. Therefore, each cross-sectional tissue slice was thought to surrogate for the corresponding tissue within 2 mm of vessel length, and surface areas of LCTCs, plaque and whole coronary segments were constructed.

In each histopathology slide, the picture image was acquired using a standard microscope and an image software (Image-Pro Plus, version 4.1, Media Cybernetics, Md.). Plaque was defined as a thickened intima with Type II to VI morphology as defined by the American Heart Association (AHA) classification [Stary H C et al. 1995 Circulation 92:1355-1374]. If a lipid core was identified in a slice, the thickness of a fibrous cap overlying a lipid core was measured at the thinnest site in ×100 magnification images, using the image analysis software (Image J, NIH). A lipid core was defined as a dense accumulation of extra-cellular lipid with cholesterol clefts occupying an extensive but well-defined region of the intima. A "thin" fibrous cap covering a lipid core in LCTCs was defined as a distinct layer of connective tissue with its thickness<100 μm, based on the possible ability of HYCI to differentiate this thinness of fibrous caps assessed in previous work incorporated herein by reference [Ishibashi F et al. 2007 Int J Cardiovasc Imaging 23:679-691].

Figure 1:
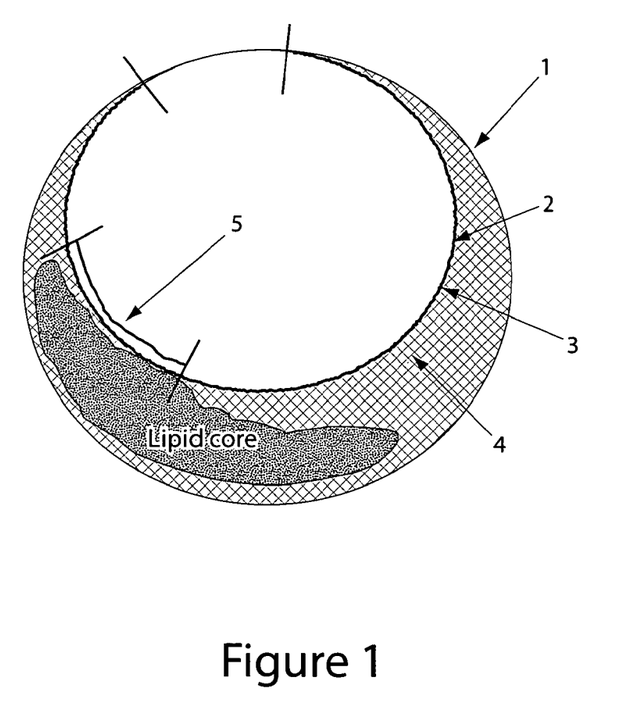
FIG. 1 is a drawing of a cross-section of a vessel showing measurement of parameters in each tissue slice: parameters labeled (1) to (3) for the construction of vessel surface images such that (1) is area of internal-elastic lamina; (2) is area of lumen; (3) circumference of lumen; and parameters labeled (4), (5) were used for the volumetric analysis, such that (4) is circumference of plaque (AHA types II-VI); and (5) is circumference of LCTC (cap thickness even less than 100 μm).

The following parameters were then measured: 1) the circumference of the lumen; 2) the length of the lumen border of plaque; and 3) the length of the lumen border of a lipid core underneath a thin fibrous cap (FIG. 1). On the constructed vessel surface, a LCTC was determined as a surface region of consecutive lipid cores underneath fibrous caps <100 μm.

To investigate the association between LCTCs and the plaque burden in segments, volumetric analysis was performed by measuring the following: 1) the area of the internal elastic lamina; and 2) the area of the lumen.

Example 5

Quantitative Colorimetry of Angioscopic Regions

The system recorded angioscopic images were acquired from the DVD player into a laptop computer (Macintosh Powerbook G4, Apple Computer, Inc. Calif.) via an analog/digital converter (ADVC-100, Canopus Co., Kobe, Japan). The display of the laptop computer was adjusted to the color temperature=CIE D65 (based on the color temperature of xenon limplight) and the gamma=2.2 (based on the definition in NTSC system) for the better visualization of image color.

A custom-made computer software for quantitative colorimetry was installed into the laptop computer, in which the known L*a*b* color space was adopted to express the color. L* describes brightness of the color (−100 to +100). A positive value of b* describes yellowness of the color (0 to 100), a negative a* blueness (−100 to 0). In previous analysis [Ishibashi F et al. 2007 Int J Cardiovasc Imaging 23:679-691] showed the impact of variables unique to angioscopy on color perception, such as intensity of light, distance, and angle [Lehmann KG et al. 1998 Cathet Cardiovasc Diagn 45:191-201; Miyamoto A et al. 2004 Clin Cardiol 27:9-15] could be minimized by adjusting for brightness L*.

Example 6

Determination of Angioscopic Region of Interest (ROI)

Angioscopic ROIs corresponding to LCTC regions were determined by matching the location in the segments or the morphology of vessels, such as stenosis, configuration, branch, thrombus or disruption. The angioscopy movie images, the histopathology picture images of tissue slices and the constructed vessel surface images were used altogether.

To analyze the sensitivity and specificity of HYCI for LCTCs, the ROIs corresponding to non-LCTC regions were also collected from the coronary segments without LCTCs. Each ROI was evaluated on the laptop computer for visual surface color (yellow or white plaque) and thrombus as previously described [Okamatsu K et al. 2004 Circulation 109:465-470; Takano M et al. 2005 J Am Coll Cardiol 45:652-658]. Angioscopic images showing the ROIs were saved as single frame images (bitmap format), and the tissue slices corresponding to ROIs (2-10 slices) were determined.

Two investigators performed quantitative colorimetry blinded to the histopathologic findings. In a saved image, a ROI was delineated and the mean value of brightness L* was measured to confirm that it was within the established optimal range (40-80) as described in a previous study [Ishibashi F et al. 2007 Int J Cardiovasc Imaging 23:679-691]. If brightness L* in the ROI was not optimal, a different single frame image was saved and the process repeated until optimal brightness L* was confirmed in the ROI. Then, for each ROI, pixels without optimal L* values were excluded, and b* and a* value were obtained for the remaining pixels and expressed as the color of the ROI. In the same single frame image, the ROI was retraced and the measurement of color was repeated.

Intra-observer agreement for b* value and a* values obtained herein was r=0.934 and 0.935 for the first and r=0.929 and 0.915 for the second observer (p<0.0001 for all). Inter-observer agreement was analyzed using the mean value of the 2 measurements by each observer, and was r=0.912 and 0.933 (p<0.0001 for both). The mean value of the 4 analyzes by the 2 observers was expressed as (b*, a*) in an angioscopic region.

HYCI was defined as b*>23, based on the association of these color appearances with LCTCs in the previous study incorporated herein by reference [Ishibashi F et al. 2007 Int J Cardiovasc Imaging 23:679-691].

Example 7

Determination of Predominant Histologic Plaque Type of ROI

A histologic plaque type of each tissue slice was determined independently in an outsourcing laboratory (CVPath, International Registry of Pathology, Gaithersburg, Md.) based on the modified AHA classification [Virmani R et al. 2000 Arterioscler Thromb Vasc Biol 20:1262-1275]. A predominant histologic plaque type in each angioscopic region was defined as a major histologic plaque type among 2-10 corresponding tissue slices, and was finally determined in all ROIs.

Statistical analysis was performed by expressing continuous variables as mean±standard error of the mean. Group differences were assessed with the chi-square test and the Fisher exact probability test for discrete variables, and the Student's t test/Mann-Whitney U test for continuous variables. The relationship between two continuous variables was assessed with Pearson's correlation coefficient. A value of <0.05 was considered to indicate statistical significance.

Figure 2:
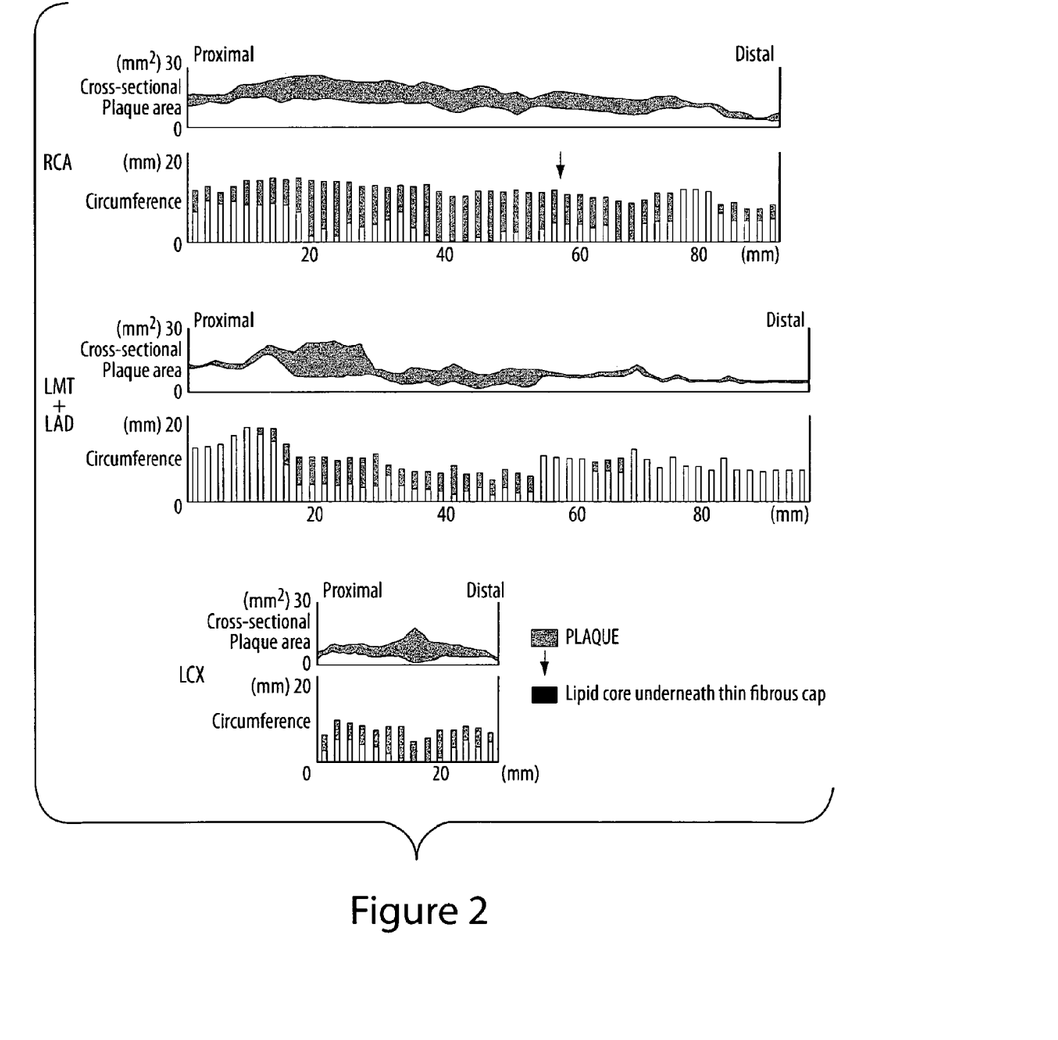
FIG. 2 is a set of data obtained from the parameters as defined in FIG. 1, describing plaque volume (upper panel) and the surface area of vessel, plaque and a lipid core underneath thin fibrous cap (lower panel) in each of coronaries (RCA=right coronary artery; LMT=left main trunk+LAD=left anterior descending artery, and LCX=left circumflex artery) of a 48 year-old male who died of acute myocardial infarction.
Figure 3:
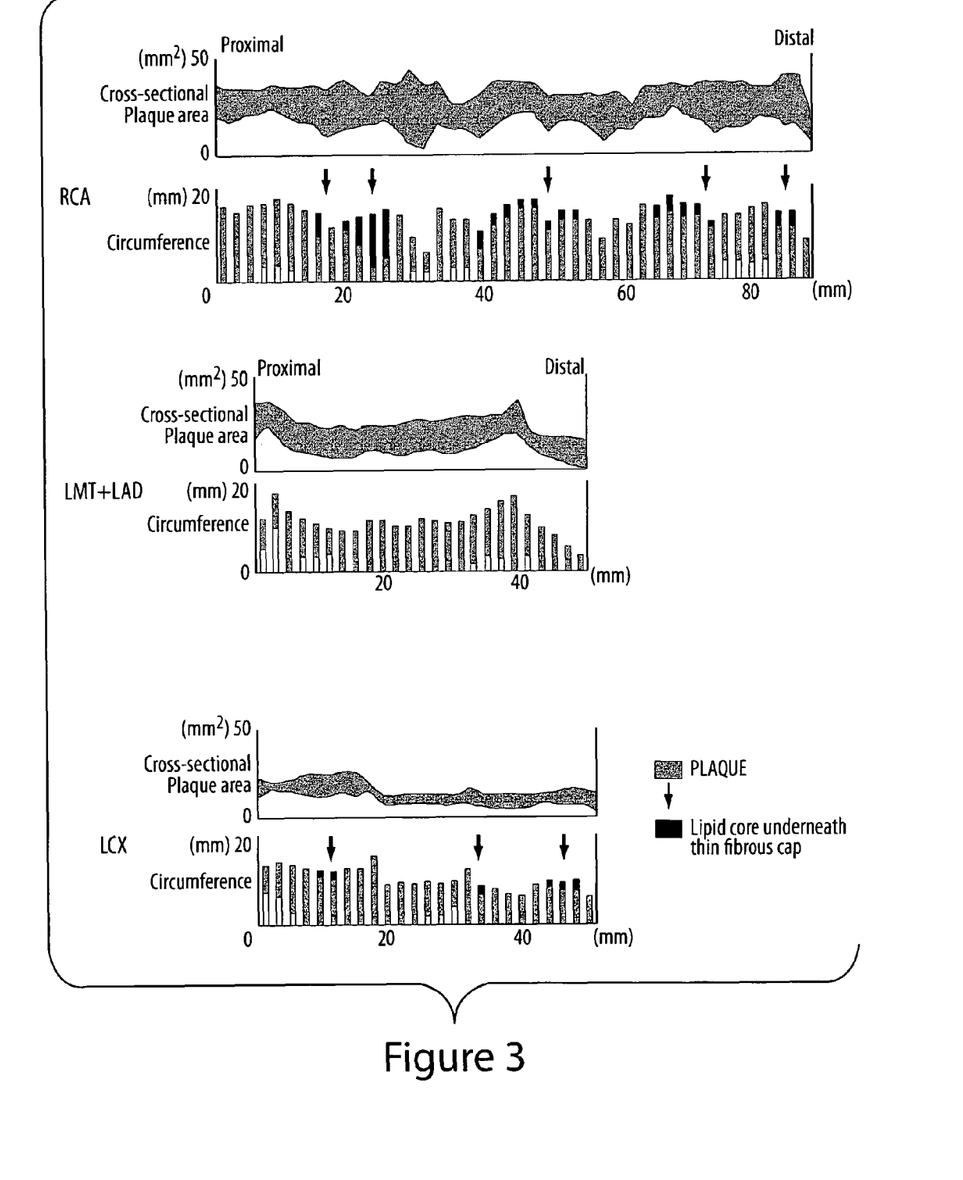
FIG. 3 is a set of data obtained from the parameters as defined in FIG. 1, for plaque volume (upper panel) and the surface area of vessel, plaque and 7 lipid cores underneath thin fibrous caps (lower panel) in each of coronaries (RCA=right coronary artery; LMT=left main trunk+LAD=left anterior descending artery; LCX=left circumflex artery) of a 59 year-old male who died of intracranial hemorrhage.

Results on the constructed vessel surface show that a total of 21 LCTCs were identified in 12 coronary segments from 9 hearts [7 RCA, 1 LMT+LAD and 4 LCX, 2.3±0.6 (1-7) LCTCs per heart]. The length and the surface area of LCTCs observed herein were 5.8±0.8 mm (2-16 mm) and 14.2±3.5 $mm^2$ (1.2-74.6 $mm^2$). The percent length and the percent surface area of LCTCs per underlying plaque were 9.4±0.4% and 2.3±0.4%, respectively (FIGS. 2, 3).

The extent of plaque (the percent length of plaque or the percent plaque surface area on the vessel surface) or the plaque burden (the mean cross-sectional plaque area in the volumetric analysis) in 12 segments with LCTCs observed herein were similar to 9 without LCTCs from the hearts with LCTCs, but were significantly higher than 19 from the hearts without LCTCs (Table 1).

TABLE 1

The extent and burden of plaque in coronary segments

|  | (1) Segments with LCTCs (n = 12) | (2) Segments without LCTCs from hearts with LCTCs (n = 9) | (3) Segments from heart without LCTCs (n = 19) | p value (1) vs. (2) | p value (1) vs. (3) |
| --- | --- | --- | --- | --- | --- |
| % length of plaque (%) | 97.2 ± 1.5 | 81.9 ± 10.1 | 58.8 ± 8.4 | 0.09 | 0.001 |
| % surface area of plaque (%) | 78.3 ± 5.1 | 60.4 ± 10.3 | 36.4 ± 6.5 | 0.11 | <0.0001 |
| Mean cross-sectional plaque area ($mm^2$) | 9.0 ± 1.1 | 6.8 ± 1.6 | 3.8 ± 0.4 | 0.26 | <0.0001 |

Values are reported as the mean ± standard error. LCTC = lipid core underneath thin fibrous cap.

The predominant histologic plaque types of LCTCs were thin-cap fibroatheroma (TCFA, n=14, 67%), fibroatheroma (n=2, 10%) and fibrocalcific plaque (n=5, 23%) (Table 2).

TABLE 2

The predominant histologic plaque types of angioscopic regions by the modified American Heart Association classification [Stary H C et al. 1995 Circulation 92:1355-1374]

|  | AIT | PIT | P | FA | TCFA | FCP | CN |
|---|---|---|---|---|---|---|---|
| Region of interest (n = 81) | 9 (11) | 16 (20) | 4 (5) | 22 (27) | 14 (17) | 14 (17) | 2 (3) |
| LCTCs (n = 21) | — | — | — | 2 (10) | 14 (67) | 5 (23) | — |
| Non-LCTCs (n = 60) | 9 (15) | 16 (27) | 4 (7) | 20 (33) | — | 9 (15) | 2 (3) |
| Yellow plaque (n = 52) | — | 9 (17) | 3 (6) | 12 (23) | 14 (27) | 14 (27) | — |
| White plaque (n = 29) | 9 (31) | 7 (24) | 1 (3) | 10 (34) | — | — | 2 (7) |
| HYCI region (n = 33) | — | 6 (18) | — | 2 (7) | 13 (39) | 12 (36) | — |
| Non-HYCI region (n = 48) | 9 (19) | 10 (21) | 4 (8) | 20 (42) | 1 (2) | 2 (4) | 2 (4) |
| HYR region (n = 20) | — | — | — | 2 (10) | 13 (65) | 5 (25) | — |
| Non-HYR region (n = 61) | 9 (15) | 16 (25) | 4 (7) | 20 (33) | 1 (2) | 9 (15) | 2 (3) |

Values are reported as n (%).
LCTCs = lipid cores underneath thin fibrous caps.
HYCI = high yellow color intensity.
HYR = higher yellow/red color intensity.
AIT = adaptive intimal thickening.
PIT = pathological intimal thickening.
FP = fibrous plaque.
FA = fibroatheroma.
TCFA = thin-cap fibroatheroma.
FCP = fibrocalcific plaque.
CN = calcified nodule.

Figure 4:
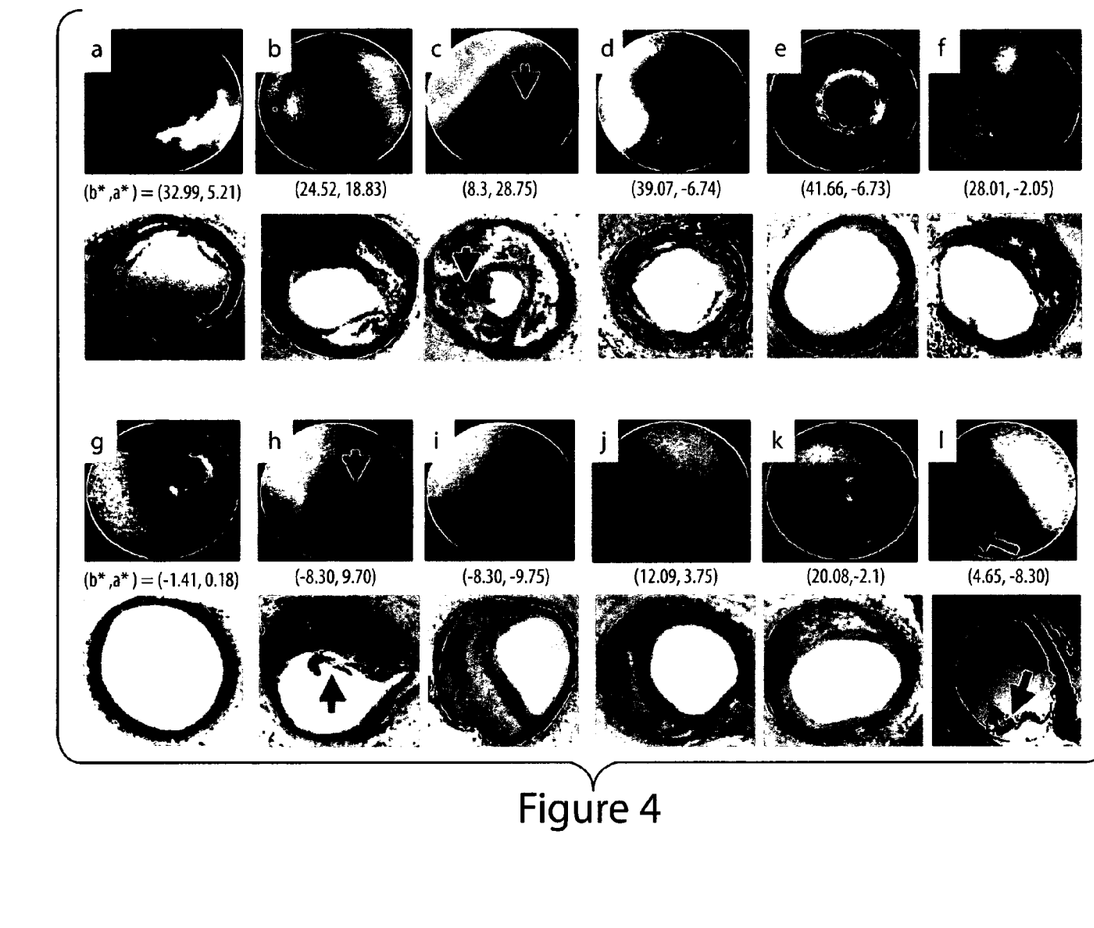
FIG. 4 is a set of photographs of representative angioscopic images corresponding to lipid cores underneath thin fibrous caps (LCTCs, panels a-d) and non-LCTCs (panels e-l). The predominant histologic plaque types in LCTCs are (panels a, b): thin-cap fibroatheroma, (panel c): fibroatheroma and (panel d): fibrocalcific plaque. In (panel c), intraplaque hemorrhage and erosion with thrombus are seen. High yellow color intensity is identified in each of panels (a), (b), (d) and (e): pathological intimal thickening with superficial foam cells and (panel f): fibrocalcific plaque with a superficial calcified lipids. Panel (g): adaptive intimal thickening. Panel (h): eroded pathological intimal thickening with thrombus. Panels (i-k): fibroatheromas with similar fibrous cap thickness, but with various tissues in fibrous caps. Panel (l): calcified nodule with thrombus.

A total of 81 angioscopic regions were determined (21 corresponding to LCTCs and 60 to non-LCTCs, FIG. 4). Yellow plaques were visually seen in 21 LCTCs and in 31 non-LCTCs. White plaques were seen in 29 non-LCTCs. The predominant histologic plaque types of yellow and white plaques were various (Table 2). Thrombus was detected in 1 yellow plaque corresponding to a LCTC (FIG. 4c) and in 2 white plaques corresponding to non-LCTCs (FIGS. 4h and 4l).

Figure 5:
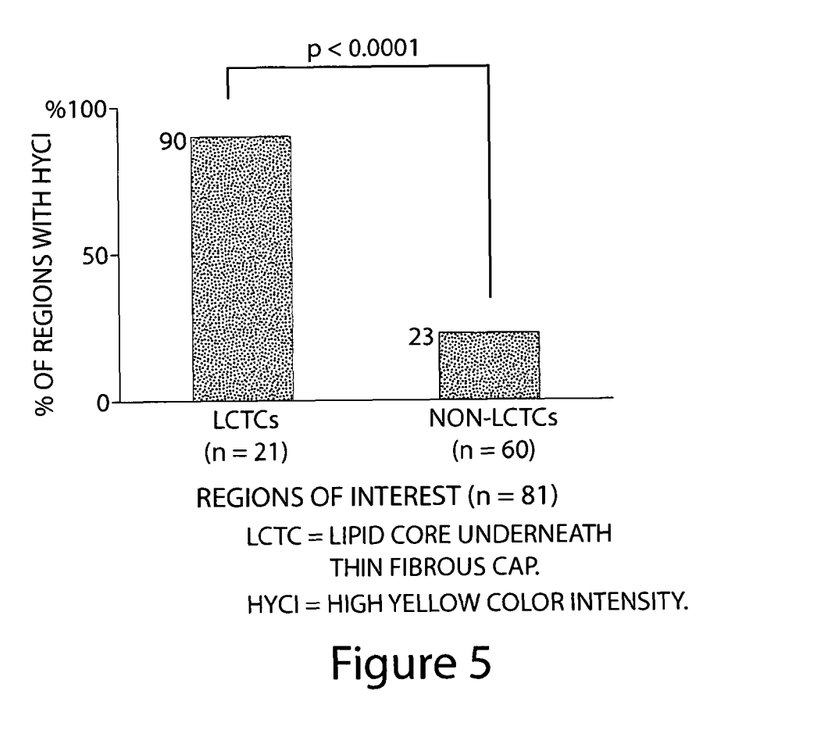
FIG. 5 is a bar graph showing the prevalence of high yellow color intensity on the ordinate, in angioscopic regions corresponding to lipid cores underneath thin fibrous caps in human coronary autopsy samples, compared to non-LCTCs.

A predefined HYCI ($b^*>23$) was more frequently identified in 19 (90%) of 21 LCTCs than in 14 (23%) of 60 non-LCTCs ($p<0.0001$, FIG. 5). The sensitivity and specificity of HYCI for LCTCs were 90% and 77%, and for TCFAs were 93% and 70%, respectively (Table 3). In 14 HYCI regions corresponding to non-LCTCs, the predominant histologic plaque types were pathological intimal thickening (n=6, FIG. 4e) and fibrocalcific plaque (n=7, FIG. 4f and Table 2). In 2 non-HYCI regions corresponding to LCTCs, intraplaque hemorrage was seen in fibroatheroma (n=1, FIG. 4c) and TCFA (n=1).

TABLE 3

Sensitivity and specificity of angioscopic color appearance for LCTCs and TCFAs

|  | Yellow plaque (n = 52) | HYCI region (n = 33) | HYR region (n = 20) |
|---|---|---|---|
| LCTCs (n = 21) | | | |
| Sensitivity (%) | 100 | 90 | 95 |
| Specificity (%) | 48 | 77 | 97 |
| Positive predictive value (%) | 40 | 58 | 90 |
| Negative predictive value (%) | 100 | 95 | 98 |
| TCFAs (n = 14) | | | |
| Sensitivity (%) | 100 | 93 | 93 |
| Specificity (%) | 43 | 70 | 90 |
| Positive predictive value (%) | 27 | 39 | 65 |
| Negative predictive value (%) | 100 | 97 | 98 |

LCTC = lipid core underneath thin fibrous cap.
TCFA = thin-cap fibroatheroma.
HYCI = high yellow color intensity.
HYR = high yellow/red color intensity.

Figure 6:
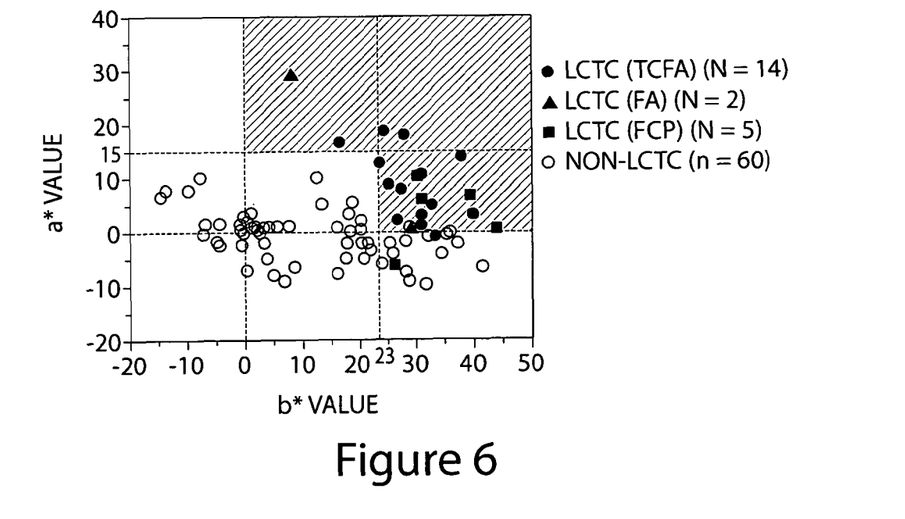
FIG. 6 is a distribution plot of the color appearance of coronary regions expressed by the quantitative colorimetric method based on the L*a*b* color space during angioscopy, with a* value shown on ordinate and b* value on the abscissa. Coronary lipid cored underneath thin (<100 μm) fibrous caps may be reliably expressed as high yellow/red color intensity (shaded area) regions.

The color values of angioscopic regions measured by the quantitative method are shown in FIG. 6. In 21 regions corresponding to LCTCs, the color ($b^*$, $a^*$) was (29.48±1.52, 7.04±1.52). Among 33 HYCI regions, $a^*$ value was significantly higher in 19 LCTCs (6.53±1.51) than in 14 non-LCTCs (−3.96±0.91, $p<0.0001$), and the cut-off $a^*$ value for LCTCs was 0 from the receiver operating characteristics curve. Among the rest non-HYCI regions, $a^*$ values were >15 in 2 LCTCs. Thus in 81 regions, the sensitivity and specificity of ($b^*>23$, $a^*>0$) or ($b^*>0$, $a^*>15$) (shaded area in FIG. 6) for LCTCs were 95% and 97%, and for TCFAs were 93% and 90%, respectively.

In non-severely stenotic human coronary artery autopsy specimens analyzed herein, HYCI regions were observed to be associated with LCTCs, and high yellow/red color intensity was the specific and sensitive angioscopic appearance of coronary LCTCs by the quantitative colorimetric analysis.

These findings show the utility of analyzing and quantifying high yellow/red color intensity to characterize coronary LCTCs. The association of LCTCs with predominant histologic plaque types is consistent with our previous study [Ishibashi F et al. 2007 Int J Cardiovasc Imaging 23:679-691], in which fibroatheroma or fibrocalcific plaque by the AHA classification were found in LCTCs, and these plaque types are associated with lipid cores [Stary H C et al. 1995 Circulation 92:1355-1374; Virmani R et al. 2000 Arterioscler Thromb Vasc Biol 20:1262-127]. Intimal cholesterol in lipids contains yellow-colored β-carotene [Blankenhom D H et al. 1956 J Clin Invest 35:1243-1247], and surface yellow color of atherosclerotic plaques is suggested to surrogate for the presence of β-carotene within 300 μm in depth [Miyamoto A et al. 2004 Clin Cardiol 27:9-15], therefore, yellow color seen during coronary angioscopy could be a surrogate for intimal lipids. This is compatible with the association of yellow plaques with histologic plaque types that usually have intimal lipids [Virmani R et al. 2000 Arterioscler Thromb Vasc Biol 20:1262-1275], and with prior descriptions [Haust M D 1983 Silver M D ed. Cardiovascular pathology. New York, N.Y.: Churchill Livingstone Inc. 191-315] of gross appearance of lipid cores, "yellow softening", or atheromatous plaques, "the fibrous cap may become extremely thin and thus the lesion may appear yellow rather than white".

However in non-severely stenotic coronary segments, HYCI had a relatively low specificity for LCTCs, which is perhaps because superficial dense lipids without necrosis or superficial calcified lipids could also appear HYCI, given the corresponding histologic plaque types [Virmani R et al. 2000 Arterioscler Thromb Vasc Biol 20:1262-1275]. Thus in coronary arteries, HYCI is likely to correlate with infiltration of lipids into the intimal surface, not only of lipid cores but also of the other forms of lipids (i.e., superficial-lipid-rich regions).

In addition to HYCI, results herein demonstrate that the reddish appearance of LCTCs is useful to discriminate LCTCs in HYCI regions. Red color intensity in LCTCs is compatible with Arakawa et al. demonstrating laser-induced fluorescent spectrum with longer wavelength (red shifts) in lipid cores compared to normal tissues [Arakawa K et al. 2002 Arterioscler Thromb Vasc Biol 22:1002-1007], and may surrogate for red colored iron (contained within hemorrhage that is likely to be associated with the increased free-cholesterol in lipid cores [Small D M 1988 Atherosclerosis 8:103-129; Kolodgie F D et al. 2003 N Eng J Med 349:2316-2325]) or lycopene (a red carotenoid in atherosclerosis [Goulinet S et al. 1997 Arterioscler Thromb Vasc Biol 17:786-796]). Thus, the appearance of coronary LCTCs during angioscopy was determined objectively by the quantitative colorimetric method provided herein as high yellow/red color intensity. It may be similar to glistening-yellow [Uchida Y et al. 1995 Am Heart J 130:195-203] or dark-yellow [Takano M et al. 2003 J Am Coll Cardiol 42:680-686] in the prior clinical angioscopic studies.

Despite the association of lipid cores underneath thin fibrous caps with culprit lesions underlying ACS [Libby P et al. 2006 J Am Coll Cardiol 48:A33-46], the variety of these plaques in space and time in coronaries has not been well determined in patients with ACS [Libby P 2005 J Am Coll Cardiol 45:1600-1602; Waxman S et al. (2006) Circulation 114:2390-2411]. In postmortem patients with acute myocardial infarction, multiple TCFAs were found by light-microscopy [Mauriello A et al. 2005 J Am Coll Cardiol 45:1585-1593]. Living patients have been found to have multiple complex lesions by angiography [Goldstein J A et al. 2000 N Engl J Med 343:915-922], multiple ruptured plaques by intravascular ultrasound [Rioufol G et al. 2002 Circulation 106: 804-808; Schoenhagen P et al. 2003 Arterioscler Thromb Vasc Biol 23: 1895-1900; Hong M K et al. 2004 Circulation 110: 928-933; Tanaka A et al. 2005 Am Coll Cardiol 45: 1594-1599] and multiple yellow plaques by angioscopy [Asakura M et al. 2001 J Am Coll Cardiol 37:1284-1288], which are consistent with the diffuse nature of atherosclerosis [Libby P et al. 2006 J Am Coll Cardiol 48:A33-46]. The association between LCTCs and coronary plaque is also consistent with the common findings of focal lipid-rich atheromas in diffuse atherosclerosis. However, the morphologies previously described by several modalities in patients with ACS [Mauriello A et al. 2005 J Am Coll Cardiol 45:1585-1593; Goldstein J A et al. 2000 N Engl J Med 343:915-922; Rioufol G et al. 2002 Circulation 106:804-808; Schoenhagen P et al. 2003 Arterioscler Thromb Vasc Biol 23: 1895-1900; Hong M K et al. 2004 Circulation 110: 928-933; Tanaka A et al. 2005 Am Coll Cardiol 45: 1594-1599; Asakura M et al. 2001 J Am Coll Cardiol 37:1284-1288] are not necessarily identical to lipid cores underneath thin fibrous caps within the coronary arterial wall. The results herein indicate that the temporal and spatial prevalence of lipid cores underneath thin fibrous caps may not necessarily be multiple in patients with diffuse coronary plaque.

HYCI determined by the quantitative colorimetric method during angioscopy, was associated with LCTCs in human coronary artery autopsy specimens. Coronary LCTCs may be reliably characterized as high yellow/red color intensity regions by angioscopy with quantitative colorimetry. Coronary angioscopy may be used to study the association of coronary lipid cores underneath thin fibrous caps with high-risk patients related to ACS.

What is claimed is:

1. A method for detecting lipid cores underneath thin fibrous caps (LCTC) and thin-cap fibroatheromas (TCFA) in a subject, the method comprising:
   identifying during an angioscopy examination of the subject a plurality of coronary or arterial plaques that form a plaque deposit in the subject:
   measuring location, morphology, size and thickness of the plaque deposit using angioscopy image data and a quantitative colorimetric method;
   applying the quantitative colorimetric method to measure coronary or arterial plaque color comprising $L^*a^*b^*$ color space determinants visible in a white light to the human eye within a $L^*a^*b^*$ color space during the angioscopy examination, wherein angioscopically-detected values of red color and yellow color are converted to the $L^*a^*b^*$ color space determinants; and
   detecting the lipid cores underneath the LCTC and TCFA in the subject having the value of $a^*$ greater than 0 and the value of $b^*$ greater than or equal to 23 in the plaque deposit of the subject, or if the value of $a^*$ is greater than or equal to 15 and the value $b^*$ is greater than 0 in the plaque deposit of the subject and $L^*$ having a value of 35 to 90.

2. The method according to claim 1, further comprising after applying the quantitative colorimetric method, comparing the values of red color and yellow color to respective values for positive controls having at least one condition selected from the group consisting of acute coronary syndrome, LCTC and TCFA.

3. The method according to claim 1, further comprising after applying the quantitative colorimetric method, comparing the values of red color and yellow color to respective values for negative controls lacking a history of at least one condition selected from the group consisting of coronary or arterial syndromes, LCTC and TCFA.

4. The method according to claim 1, wherein applying the quantitative colorimetric method further comprises an adjustment for brightness ($L^*$ value) to overcome variable factors that affect the results in the angioscopy, wherein the variable factor is at least one factor selected from the group consisting of intensity of light, angle and distance.

5. The method according to claim 1, wherein the angioscopy is performed in a subject in vivo.

6. The method according to claim 1, wherein the angioscopy is performed in explanted cardiac tissue of a coronary autopsy sample and lipid cores are detected.

7. A computer program embedded in a non-transitory computer readable medium that is adapted to carry out a quantitative colorimetric method comprising;
acquiring angioscopy data, analyzing the angioscopy data by applying L*a*b* color space determinants visible in a white light to the human eye within a L*a*b* color space to the angioscopv data, wherein angioscopically-detected values of a red color and a yellow color yield a quantitative colorimetric parameter; and detecting lipid cores underneath thin fibrous caps (LCTC) and thin-cap fibroatheromas (TCFA)-(TCFA) in a plaque deposit using the quantitative colorimetric parameter, wherein the value of a* is greater than 0 and the value of b* is great than or equal to 23 detects the lipid cores in a plaque deposit in the subject; or the value of a* is greater than or equal to 15 and the value of b* is greater than 0 and L* has a value of 35 to 90 detects the lipid cores in the plaque deposit in the subject; or the value of a * is greater than or equal to 15 the value of b* is greater than 0 L * has a value of 35 to 90 detects the lipid cores in the plaque deposit in the subject.

8. In a method for analyzing colorimetric angioscopy, the improvement comprising acquiring angioscopy data, applying a quantitative colorimetric method to the angioscopy data to measure coronary plaque color using L*a*b* color space determinants visible in a white light to the human eye within a L*a*b* color space, wherein angioscopically-detected values of red color and yellow color yield a quantitative colorimetric parameter to detect lipid cores underneath thin fibrous caps LCTC and thin-cap fibroatheromas TCFA in the subject, wherein the value of a* is greater than 0 and the value of b* is greater than or equal to 23 detects the lipid cores in the plaque of the subject, or wherein the value of a* is greater than or equal to 15 and the value of b* is greater than 0 and L* has a value of 35 to 90 detects the lipid cores in the plaque of the subject.

9. The method according to claim 1, wherein the subject is a male.

10. The method according to claim 9, wherein the subject is human.

11. The method according to claim. 1, wherein the subject is female.

12. The method according to claim 11, wherein the subject is post-menopausal or peri-menopausal, 13. A method for screening a plurality of test compounds to identify a modulator of formation of a plurality of coronary lipid core underneath thin fibrous caps (LCTC) or thin-cap fibroatheroma (TCFA) for administering to a subject at risk for a condition, the method comprising:
providing a plurality of non-human experimental animal subjects having coronary lipid core underneath thin fibrous caps (LCTC) or thin-cap fibroatheroma (TCFA);
administering to a portion of the animals at least one test compound, and administering to another portion of the animals a control lacking the compound;
angioscopically detecting values of red color and yellow color in arteries or other vascular tissue of the animals; and
converting the values to L*a*b* color space determinants visible in a white light to the human eye within a L*a*b* color space;
wherein the angioscopically detected values of red color and yellow color detects lipid cores underneath the LCTC and TCFA in the subject from the value for each of the L*a*b* color space determinants if the value of a* is greater than 0 and the of b* is greater than or equal to 23 in a plaque deposit of the subject, or if the value of a* is greater than or equal to 15 and the value of b* is greater than 0 in the plaque deposit of the subject and L* has a value of 35 to 90, wherein the test compound that yields lower values of red color and yellow color in the L*a*b* color space in the portion of the animals administered the test compound compared to the portion of the animals administered the control is identified as the modulator of the lipid core underneath the LCTC and TCFA.

14. The method according to claim 1, wherein * has a value of 40 to 80.

15. The method according to claim 14, wherein the subject is diagnosed as having at least a 90% risk of disruption, thrombosis, or an acute coronary syndrome.

16. The computer program according to claim 7, wherein angioscopy data are obtained from a subject that is male.

17. the computer program according to claim 7, wherein angioscopv data are obtained from a subject that is female.

* * * * *